United States Patent
Nixon et al.

(10) Patent No.: US 6,645,196 B1
(45) Date of Patent: Nov. 11, 2003

(54) GUIDED TOOL CHANGE

(75) Inventors: Thomas Robert Nixon, Sunnyvale, CA (US); William C. Nowlin, Los Altos, CA (US); Günter D. Niemeyer, Mountain View, CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 281 days.

(21) Appl. No.: 09/595,777

(22) Filed: Jun. 16, 2000

(51) Int. Cl.[7] ............................................ A61B 17/00
(52) U.S. Cl. ......................... 606/1; 606/130; 128/898; 318/568.11
(58) Field of Search ........................... 606/1, 130, 139; 74/490.11, 490.12; 318/568.11, 568.21; 128/898

(56) References Cited

U.S. PATENT DOCUMENTS

| | | |
|---|---|---|
| 4,791,934 A | 12/1988 | Brunnett |
| 4,837,703 A | 6/1989 | Kakazu et al. ......... 364/474.18 |
| 5,230,338 A | 7/1993 | Allen et al. |
| 5,343,385 A | 8/1994 | Joskowicz et al. ..... 364/167.01 |
| 5,417,210 A | 5/1995 | Funda et al. ............. 128/653.1 |
| 5,528,955 A * | 6/1996 | Hannaford et al. ...... 74/490.01 |
| 5,820,623 A * | 10/1998 | Ng ................................. 606/1 |
| 6,325,808 B1 * | 12/2001 | Bernard et al. ............. 606/139 |

* cited by examiner

Primary Examiner—Michael J. Milano
Assistant Examiner—Julian W. Woo
(74) Attorney, Agent, or Firm—Townsend and Townsend and Crew LLP

(57) ABSTRACT

A guided tool change procedure is employed in minimally invasive robotic surgery to guide a new tool quickly and precisely, after a tool change operation, back into close proximity to the operating position of the original tool prior to its removal from the surgical site. A first robotic surgical tool is placed at an operating position inside the cavity using a slave manipulator disposed outside the cavity, and the operating position is recorded. The first robotic surgical tool is decoupled from the slave manipulator and removed from the cavity. A second robotic surgical tool is introduced into the cavity. Based on the recorded operating position, a target space is derived for placing the distal end of the second robotic surgical tool in close proximity to the location of the distal end of the first robotic surgical tool in the operating position prior to its removal from the cavity. A controller is provided to control the slave manipulator to guide the distal end of the second robotic surgical tool, during insertion of the second tool, to a location within the target space.

33 Claims, 13 Drawing Sheets

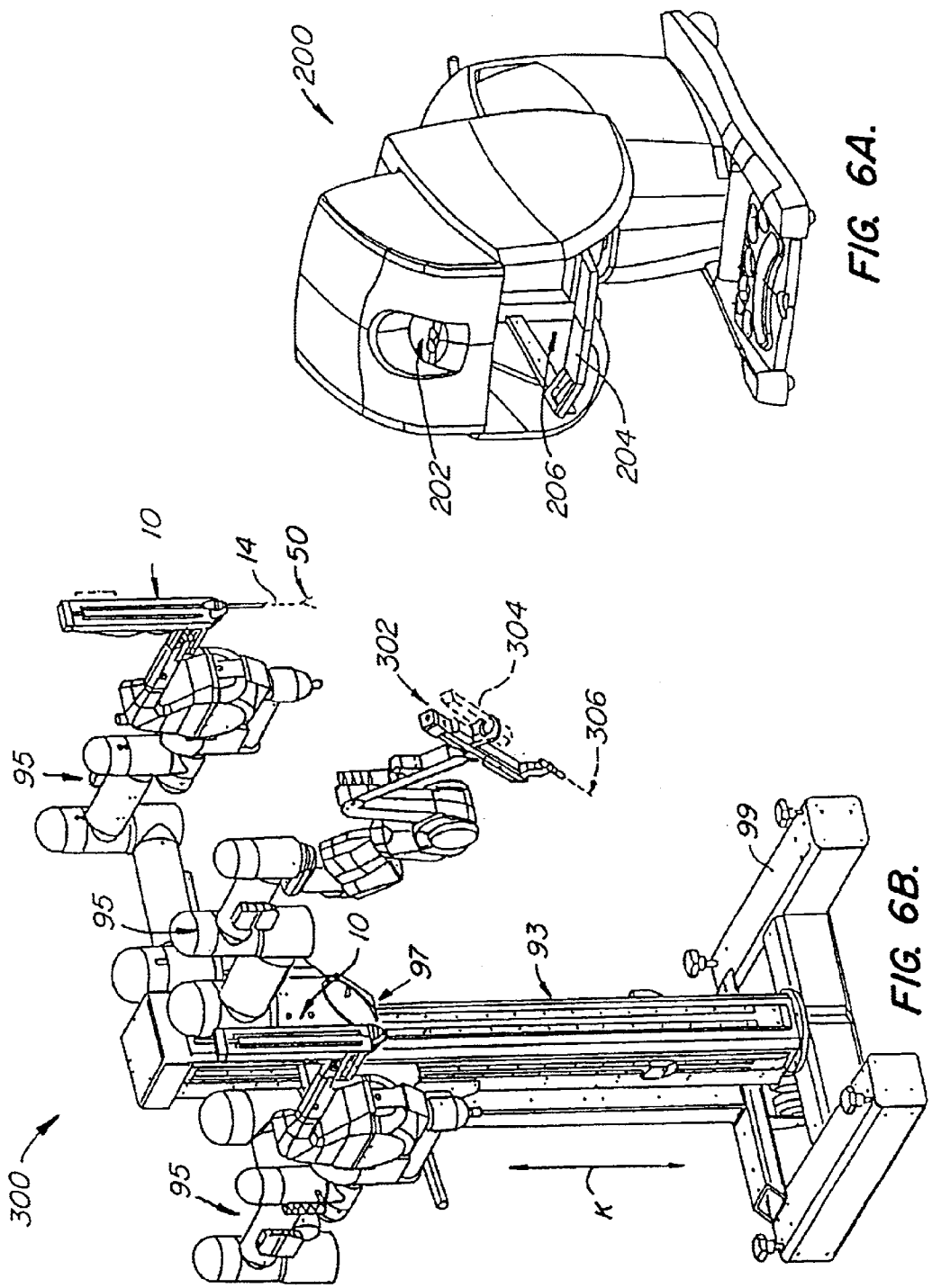

GUIDED TOOL CHANGE

CROSS-REFERENCES TO RELATED APPLICATIONS

This application is related to the following patents and patent applications, the full disclosures of which are incorporated herein by reference: PCT International Application No. PCT/US98/19508, entitled "Robotic Apparatus", filed on Sep. 18, 1998, U.S. application Ser. No. 09/418,726, entitled "Surgical Robotic Tools, Data Architecture, and Use", filed on Oct. 15, 1999; U.S. Application Serial No. 60/111,711, entitled "Image Shifting for a Telerobotic System", filed on Dec. 8, 1998; U.S. application Ser. No. 09/378,173, entitled "Stereo Imaging System for Use in Telerobotic System", filed on Aug. 20, 1999; U.S. application Ser. No. 09/398,507, entitled "Master Having Redundant Degrees of Freedom", filed on Sep. 17, 1999, U.S. application Ser. No. 09/399,457, entitled "Cooperative Minimally Invasive Telesurgery System", filed on Sep. 17, 1999; U.S. application Ser. No. 09/373,678, entitled "Camera Referenced Control in a Minimally Invasive Surgical Apparatus", filed on Aug. 13, 1999; U.S. provisional application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument that is manipulatable for effecting a predetermined treatment of a target tissue, and can include clamps, graspers, scissors, staplers, and needle holders, for example. The terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment of a target tissue in the surgical site. The instrument or tool typically includes a shaft carrying the end effector(s) at a distal end, and is preferably servomechanically actuated by a telesurgical system for performing functions such as holding or driving a needle, grasping a blood vessel, and dissecting tissue.

To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

A typical surgery employs a number of different surgical instruments. When a different tool is desired during the surgical procedure, the surgical instrument is typically withdrawn from the surgical site so that it can be removed from its associated arm and replaced with an instrument bearing the desired end effector. The desired surgical instrument is then inserted into the surgical site. A surgical instrument may also be withdrawn from a surgical site for reasons other than to replace the end effector. For example, the loading of a clip in a clip applier used in affixing tissue typically occurs outside of the patient's body. Each time a new clip is desired, the clip applier is removed from the surgical site to load the clip and then reintroduced into the patient's body to apply the clip.

Tool exchange for a robotic system takes time. Moreover, it may be difficult to bring the new tool into the field of view manually after a tool change operation. It is also possible for the operator to misjudge the depth of insertion and place the tool too deep into the surgical site, which may cause unintended contact between the tool and the patient's anatomy. To avoid such contact, the operator is likely to move the new tool very slowly into the surgical site. These factors contribute to make a tool change operation a time-consuming process.

SUMMARY OF THE INVENTION

The present invention is generally directed to robotic surgery methods, devices, and systems. The invention overcomes the problems and disadvantages of the prior art by providing a guided tool change procedure to facilitate guidance of a new tool after a tool change operation back into close proximity to the operating position of the original tool prior to its removal from the surgical site. The invention does so by recording the operating position of the original tool and calculating control parameters based on the operating position and the configuration of the new tool to guide the new tool easily and precisely into the vicinity of the operating position. In this way, the tool change procedure can be safer, more accurate, and less time-consuming, thereby minimizing "down time" and risk of injury to the patient.

In accordance with an aspect of the present invention, a method of performing minimally invasive robotic surgery in a body cavity of a patient comprises recording an operating position at which a first robotic surgical tool is disposed inside the cavity. The first robotic surgical tool is removed from the cavity. The method further includes determining the desired location within the body cavity of a second robotic tool based on the recorded position of the first robotic tool. The second robotic surgical tool is introduced into the cavity and guided to the desired location in close proximity to the operating position.

In some embodiments, the second robotic surgical tool is automatically or manually guided to a target space comprising the recorded position of the first tool's distal end with the target space being defined in part by the recorded position. The target space may be defined to include a maximum allowable depth which limits the depth of insertion of the distal end of the second robotic surgical tool in the cavity. For instance, the second robotic surgical tool may be placed with the distal end disposed within a preset distance from the sensed position of the distal end of the first robotic surgical tool. The second robotic surgical tool may be introduced into the cavity substantially via a straight line from the port of entry of the cavity to the target space.

In accordance with another aspect of the invention, a method of performing minimally invasive robotic surgery in a body cavity of a patient comprises recording an operating position at which a first robotic surgical tool is disposed inside the cavity. The first robotic surgical tool is decoupled from the slave manipulator and removed from the cavity. The method further includes determining the desired position within the body cavity of a second robotic tool based on the recorded position of the first robotic tool. The second robotic surgical tool is coupled with the slave manipulator, and introduced into the cavity. The second tool is guided to the desired position in close proximity to the operating position.

In accordance with another aspect of the present invention, a surgical robotic system comprises a slave manipulator for coupling with and actuating a robotic surgical tool inside a body cavity of a patient. A controller is configured to control movement of the slave manipulator and the robotic tool, and comprises a computer. At least one sensor is coupled with the slave manipulator for sensing an operating position of the robotic surgical tool coupled with the slave manipulator. The computer includes a first set of computer instructions for controlling the slave manipulator, after the first robotic surgical tool is removed from the cavity and decoupled from the slave manipulator, to automatically position the slave manipulator so that the second robotic surgical tool can be guided to a location in close proximity to the sensed operating position.

Another aspect of the invention is a method of delivering a robotic surgical instrument having a distal tip to a surgical site. The method comprises determining, via a computer, a target space for a preset portion of the robotic surgical instrument (such as its distal tip) to occupy upon delivery to the surgical site, and guiding delivery of the instrument to the surgical site such that the instrument is delivered into the target space.

In some embodiments, the guiding delivery comprises guiding delivery of the instrument in one degree of movement along an insertion axis. The instrument comprises a proximal shaft, a wrist member movably coupled to the shaft at a first joint, and an end effector movably coupled to the wrist member at a second joint. Movement around the first and second joints provide the end effector with multiple degrees of freedom of movement relative to the shaft. The multiple degrees of movement are constrained during delivery of the instrument to the surgical site.

BRIEF DESCRIPTION OF THE DRAWINGS

FIG. 6A is a perspective view of an operator station of a telesurgical system in accordance with an embodiment of the invention;

FIG. 6B is a perspective view of a cart or surgical station of the telesurgical system according to an embodiment of the invention, the cart of this particular embodiment carrying three robotically controlled arms, the movement of the arms being remotely controllable from the operator station shown in FIG. 6A;

DESCRIPTION OF THE SPECIFIC EMBODIMENTS

The present invention is directed to providing guided tool change in minimally invasive surgery by setting up a guide path that can be used to guide a new tool, after a tool change operation, to a location in close proximity to the operating position of the original tool prior to its removal from the surgical site.

I. Guided Tool Change

Figure 1:
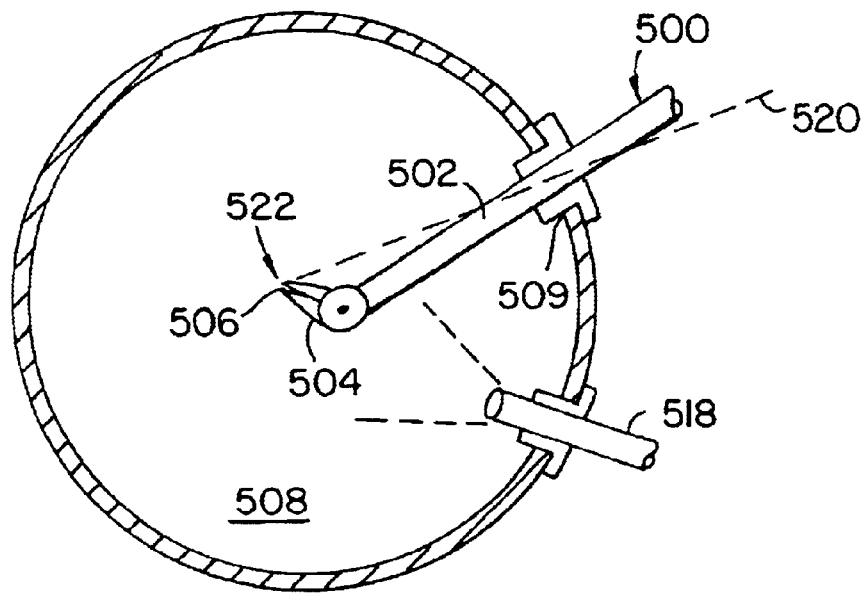
FIG. 1 is a schematic view illustrating a first surgical tool in an operating position in a surgical site.

FIG. 1 shows a surgical tool 500 including a body 502 typically in the form of a shaft and an end effector 504 having a distal end 506. The distal end 506 is typically a tool tip of the end effector 504. The tool 500 is inserted into a surgical site 508 in a cavity of a patient's body via a port of entry 509. The tool body 502 and the end effector 504 are manipulated from outside the surgical site 508 to have a particular orientation at the operating position as shown in FIG. 1. A robotic manipulator arm having one or more actuators is typically used to manipulate the surgical tool body 502 and the end effector 504.

Figure 2:
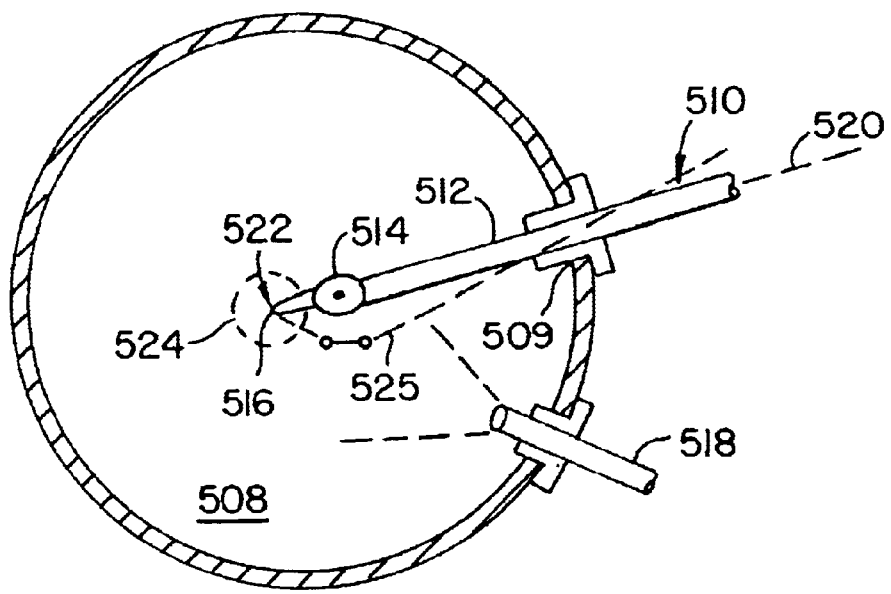
FIG. 2 is a schematic view illustrating a second surgical tool placed in close proximity to the operating position of the first surgical tool of FIG. 1 after a tool change operation.

When it is desired to remove the tool 500 from the surgical site 508 and introduce another tool 510 as shown in FIG. 2, the operating position of the tool 500 is recorded. When the other tool 510 is introduced into the surgical site 508, the recorded data of the operating position of the first tool 500 is used to provide a guide path for the second tool 510 so that it can be moved to the operating position quickly and precisely. The second tool 510 includes a body 512 and an end effector 514 with a distal end 516. Using the recorded position data, the second tool 510 can be accurately positioned at the surgical site, e.g., in a field of view of an endoscope 518 or other viewing instrument. This is a way of performing a guided tool change operation.

Typically, it is desirable to record the operating position of the distal end 506 of the first tool 500, which is then used to determine the desired position of the distal end 516 of the second tool 510. In this way, the depth of insertion of the second tool 510 can be limited by the position of the distal end 516 to prevent extending the second tool 510 too far into the surgical site 508 and causing injury to the patient, especially for a tool with a sharp tool tip. The actual position of the tool tip may be determined before or after tool withdrawal. The second tool 510 preferably may be introduced via a straight line path to position the distal end 516 in the operating position. The straight line is illustrated as an imaginary line 520 in FIG. 1 which intersects the target point 522 of the distal end 506 of the first tool 500 in the operating position. The imaginary line 520 may be used as an insertion axis guide for introducing the second tool 510 in FIG. 2, and may be referred as an in-out axis or IO axis. The 10 axis may represent a degree of freedom of movement of a tool. For instance, the tool be mounted to a carriage that is driven to translate along a linear guide formation of a robotic arm which is movable in additional degrees of freedom including angular displacements to position the tool. For comparison, the operating position of the first tool 500 prior to its removal is shown in broken lines in FIG. 2. Of course, the insertion path may be curvilinear in general, as long as the tool is positioned so as not to cause injury to the patient.

The location of the distal end 506 may be determined using sensors or the like. The sensed location is preferably used as the target point 522 to calculate parameters for controlling an actuator to manipulate the second tool 510 and guide its movement to the operating position. In a specific embodiment, the same actuator used to move the first tool 500 is used to manipulate the second tool 510 after a tool change operation.

Often, it is not necessary to place the second tool 510 with its distal end 516 at precisely the target point 522. A target space 524 may be defined in the vicinity of the target point 522 to provide an acceptable region for positioning the distal end 516, corresponding e.g., to any position within the surgeon's field of view. FIG. 2 shows a spherical target space 524 defined by specifying an acceptable distance from the target point 522 in which to place the distal end 516. Another way is to define a rectangular target space by specifying one distance along the imaginary line 520 from the target point 522 and two transverse distances perpendicular to the imaginary line 520 and to one another. Another example of a target space is a conical space or a truncated conical space defined by a yaw angle and a pitch angle of rotating the tool 510 about the port of entry 509. Of course, other ways of defining a target space 524 may be used. The use of a target space advantageously provides a safety factor to prevent extending the tool too far into the surgical site.

Figure 3:
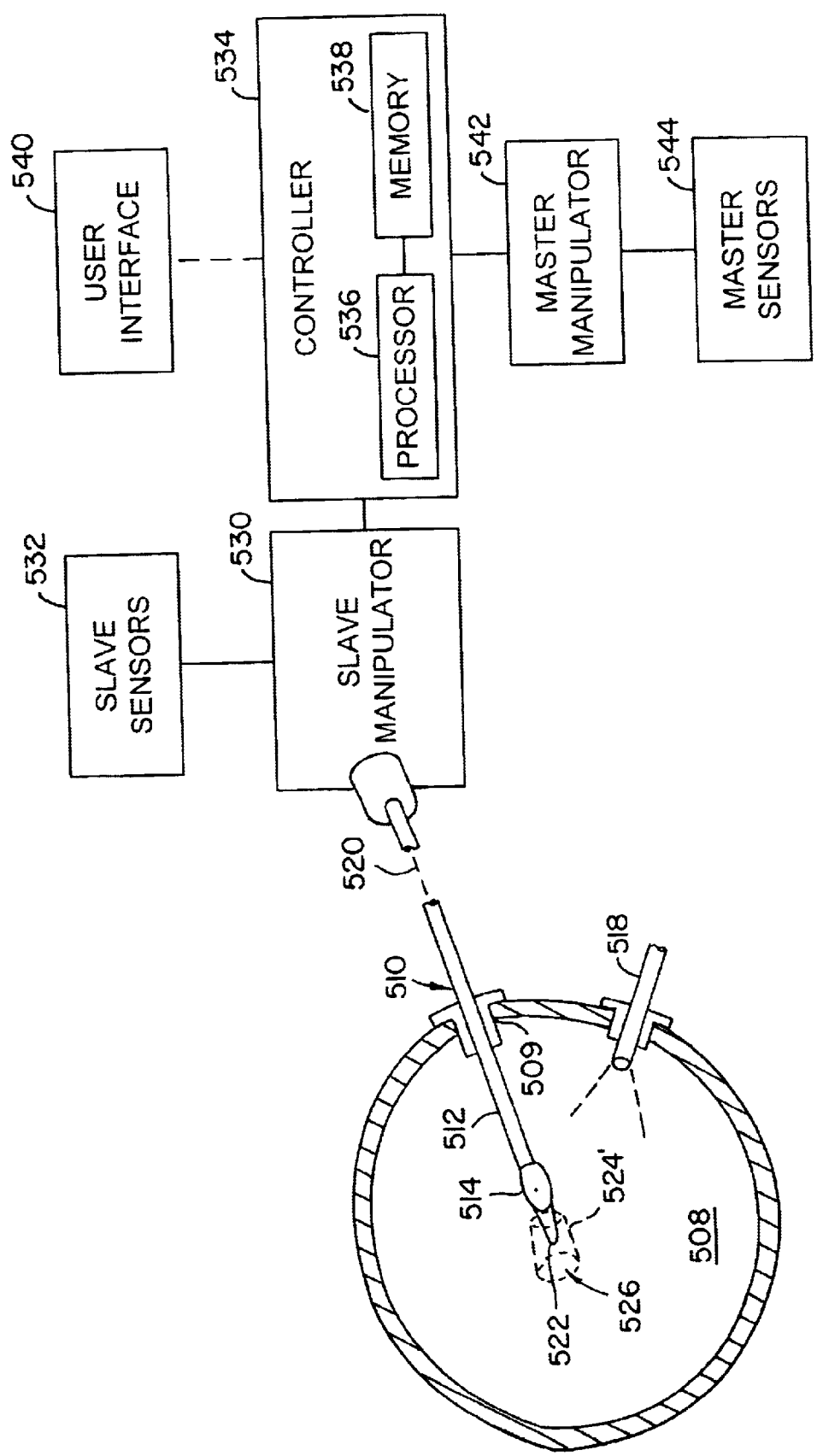
FIG. 3 is a schematic view illustrating a robotic surgical system for placing the distal end of a second surgical tool in a target space derived from the location of the distal end of the first tool in the operating position of FIG. 1.

Because it is often desirable to limit the insertion depth of the second tool 510 to prevent injury to the patient, particularly if the second tool 510 has a sharp tool tip, a virtual wall or servo wall 526 may be specified to limit the insertion depth relative to the IO axis, as illustrated in FIG. 3. The virtual wall 526 may intersect the target point 522 or may be disposed inward or outward along the imaginary line or IO axis 520 relative to the target point 522. For safety reasons, it may be desirable to move the virtual wall 526 from the target point 522 so as to reduce the insertion depth and to provide a margin of error in more reliably avoiding damage to the internal organs or tissue of the patient by the second tool 510. FIG. 3 shows a truncated conical target space 524' which is defined in part by the virtual wall 526.

FIG. 3 shows a slave manipulator 530 connected with the second tool 510 for moving the tool. The slave manipulator 530 may include a servomechanism. One or more slave sensors 532 may be provided for sensing the movement of the slave manipulator 530 and the tool 510. A controller 534 is coupled with the slave manipulator 530 for controlling operation of the slave manipulator 530. The controller 534 includes a processor 536 and a memory 538. The processor 536 typically includes analog and digital input/output boards, interface boards, and various controller boards. A user interface 540 is generally not necessary, but may be provided for receiving input instructions and displaying outputs if desired. For example, the interface 540 may include a CRT monitor and an input device such as a keyboard.

In a preferred embodiment, a master manipulator 542 is coupled with the controller 534, and one or more master sensors 544 may be provided for sensing movement of the master manipulator 542, as illustrated in FIG. 3. The master manipulator 542 is moved by a human operator such as a surgeon. Based on movement of the master manipulator 542, the controller 534 maps the movement of the tool 510 and the slave manipulator 530 onto the movement of the master manipulator 542.

The controller 534 desirably is capable of calculating the control parameters for moving the slave manipulator 530, based on the operating position of the first tool 500 prior to its removal from the surgical site 508 and the configurations and dimensions of the first and second tools 510, to automatically set up a target space 524 in which to place the second tool 510 so that the second tool 510 (more particularly, the distal end 516) is in close proximity to the operating position of the first tool 500. The controller 534 controls the operation of the manipulators 530, 542 by executing system control software, which is a computer program stored in a computer-readable medium such as the memory 538. The memory 538 is typically preferably a non-volatile re programmable "flash" memory. The computer program includes sets of instructions that dictate the mapping operation of the surgical tool onto the master and the guided tool change operation. The computer program code can be written in any known computer readable programming language.

Figure 4:
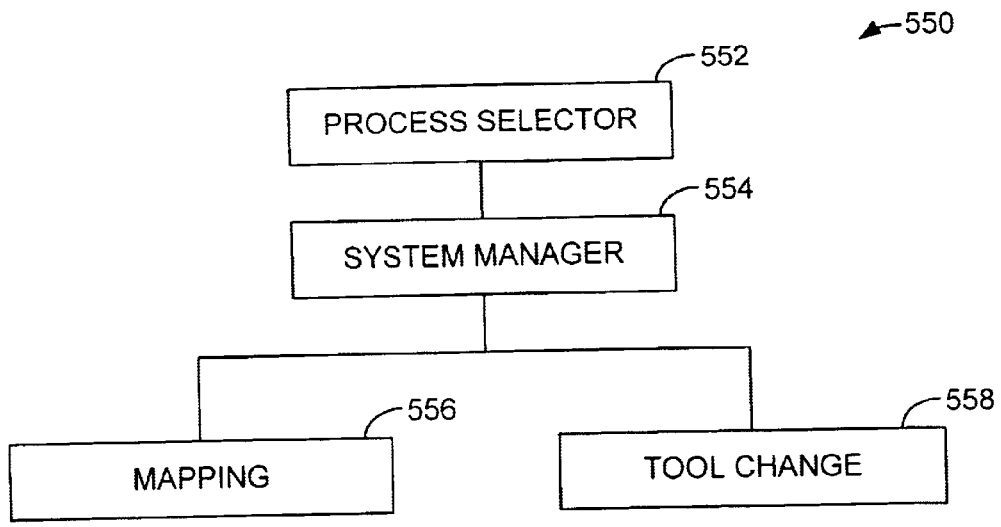
FIG. 4 is a block diagram of a hierarchical control structure of the system control software for controlling operation of the robotic surgical system of FIG. 3.

FIG. 4 is a block diagram of an embodiment of the hierarchical control structure of the system control software or computer program 550. Input parameters and instructions entered into the user interface 540 are supplied to a process selector 552 for performing a mapping operation or a guided tool change operation or any other desired operations. A system manager subroutine 554 comprises program code for accepting the specified parameters for the particular operation from the process selector subroutine 552 and controlling the operation of the robotic system shown in FIG. 3. The system manager subroutine 554 controls execution of a number of subroutines that control operation of the manipulator 530, 542. For example, FIG. 4 shows a mapping subroutine 556 and a tool change subroutine 558. The system manager subroutine 554 controls the operation of the robotic system according to the mapping mode or the tool exchange mode.

In the mapping mode, the mapping subroutine 556 has program code for processing information received from the master sensors 544 representing movement of the master manipulator 542 to produce control signals to be supplied to the slave manipulator 530 for mapping the movement of the tool 510 coupled with the slave manipulator 530 to the movement of the master manipulator 542. An example of a mapping scheme is disclosed in U.S. application Ser. No. 09/373,678, entitled "Camera Referenced Control in a Minimally Invasive Surgical Apparatus", filed on Aug. 13, 1999, which is fully incorporated herein by reference.

In the guided tool change mode, the movements of the slave and master are no longer locked. The tool change subroutine 558 has program code for processing information received from the slave sensors 532 representing the movement and position of the slave comprised of the slave manipulator 530 and the first tool 500.

The general introduction of an instrument into a body cavity, such as for use during endoscopic surgery, requires motion in one or more degrees of freedom. Similarly, there are complementary degrees of freedom during instrument introduction that may be constrained. In the presently-described preferred embodiment, a single degree of freedom—a corresponding to motion along the insertion axis—is available, while all other degrees of freedom are constrained, particularly the other two proximal degrees of freedom of movement, used to position the tool mount before reinsertion, and the distal degrees of freedom of movement associated with the instrument's wrist joint and end effector. These degrees of freedom are released for movement by the surgeon operator once operative connectivity between the master controls and the slave manipulator and tool is reestablished, preferably after tool exchange is completed. Additionally, in the preferred embodiment, the unconstrained degree of freedom constitutes a linear axis of movement coinciding exactly with one joint of the tool mount mechanism. None of these elements of the present preferred embodiment, however, should be understood to constrain the general scope of the present invention, as described below.

In general, to describe a guided tool change, one identifies some degrees of freedom of movement that are free to move, with the remaining degrees of freedom of movement either absolutely or substantially constrained, via servo control or the like, so as not to move or to resist motion, respectively, in that direction. Furthermore, separation of the configuration space into a free space and a constrained space may represent any hypersurface of convenient shape as determined to be of interest to the designers or the surgeons. That is to say, the free and constrained subspaces may be (1) aligned or not aligned with any available coordinate system, including the natural coordinates associated with the tool mount mechanism design, Cartesian coordinates, spherical coordinates, or other coordinate systems as a matter of convenience and appropriateness, and (2) programmable in the factory or before surgery, or reprogrammable during surgery by identifying the free and constrained degrees of freedom via an appropriate user interface. The path representing the unconstrained degrees of freedom may be chosen using pre- or intra-operative data (e.g., CT scans, ultrasound, anatomical models or the like), and introduced into the system controlling the mechanism through an appropriate user interface. Using such information, guided tool change may operate without storing information about a first tool before removal, and may operate without removal of a first tool.

Preferably, the constraints constitute a less than rigid, or somewhat "soft," barrier, such as a saturating spring simulation implemented via a backdrivable servo mechanism. It may be appreciated that the stiffness of the constraint presented to the operator is a matter of implementation detail, and does not materially change the essential idea of providing a virtual guide channel through which the instrument is delivered to the surgical site.

Likewise, the end of the guide path may be implemented by describing a hypersurface in the space of the unconstrained degrees of freedom. While those degrees of freedom are unconstrained on one side of the surface, they are constrained by the mechanism from passing to the other side of the surface. It will be appreciated that although motion in the free space is described as without resistance, it may be limited in speed, in direction, or modified or resisted in other ways without disturbing the separation of free and constrained spaces.

Finally, any arbitrary subspace of all degrees of freedom, such as a cube, a sector of a cone, or indeed any described shape, may be chosen to indicate the target space. Entry of the tip into this target space, as sensed by the mechanism, indicates the end of the guided tool change. Transfer of control back to the operator is then provided, either automatically or by indicating that the surgeon operator can acquire control by taking some action, e.g., by actuating an end effector or by pressing an input button if tool delivery to the surgical site is not automated, e.g., via a surgeon's assistant. It will be appreciated that other criteria may also indicate the end of the guided tool change. These include the location of other points on the tool in other target spaces, the location of joints in some predefined or precomputed regions, other sensor inputs, for example, visual or image based detection of the tool, or explicit user input.

Figure 4A:
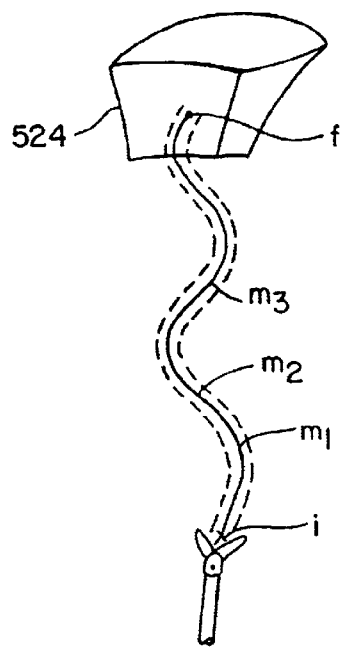
FIG. 4A is a schematic view illustrating a guided tool path.

To understand how such a general tool change would be beneficial, the following description of a guided tool change using general constraint equations is helpful. Let $\theta_i$ represent a set of coordinates of convenience, with $\theta_1$ (without loss of generality) representing the depth of insertion past a reference point such as the remote center or port of entry into the patient's body. A one-dimensional guide path is described by the continuum of points given by the function $(\theta_1, \theta_2, \ldots \theta_n) = (\theta_1, f_{\theta 2}(\theta_1), \ldots, f_{\theta 3}(\theta_1), f_{\theta n}(\theta_1))$ where $f_{\theta i}$ are continuous functions of the $\theta_1$ coordinate. A multidimensional guide path is a natural extension of this concept: generally the first k variables are free, and the remaining n-k variables are constrained. The mechanism or its computer control is then designed to provide constraints that guide the tool tip so that it always lies at some point on that path. The description then proceeds: (1) The tool mount adjusts so that the tool is initially guided to intersect point (i) in FIG. 4A. Point i represents the beginning of the constrained path. (2) As the assistant inserts the tool, the tool mount control system continually (2a) realigns the tool mount guide to pass through point ($m_1$), then ($m_2$), then ($m_3$), by continually adjusting the guide as the tip moves along the continuum of points of the like until it reaches the target space 524 in FIG. 4A. In the preferred embodiment, the coordinates of the tool mount mechanism correspond to point (i), and θ1 is the only free variable corresponding to the insertion axis. It will be appreciated that the multidimensional guide path based on the coordinates $θ_i$ need not only define a path for the distal tip of the too, but may also define a path for other points along the tool or joints in the mechanism to create any complex path, including, for example, serpentine paths.

In this manner, using a robotic or telerobotic system to implement a constraint while permitting the user to introduce the instrument to the surgical site along an arbitrary curvilinear path is made possible. Again, while the preferred embodiment describes an arrangement in which the arbitrary path is linear, a curvilinear path could be used, for example, to have the slave manipulator guide an inserted tool around a portion of the patient's anatomy in order to reach the surgical site without adversely affecting that portion of the anatomy.

Figure 5:
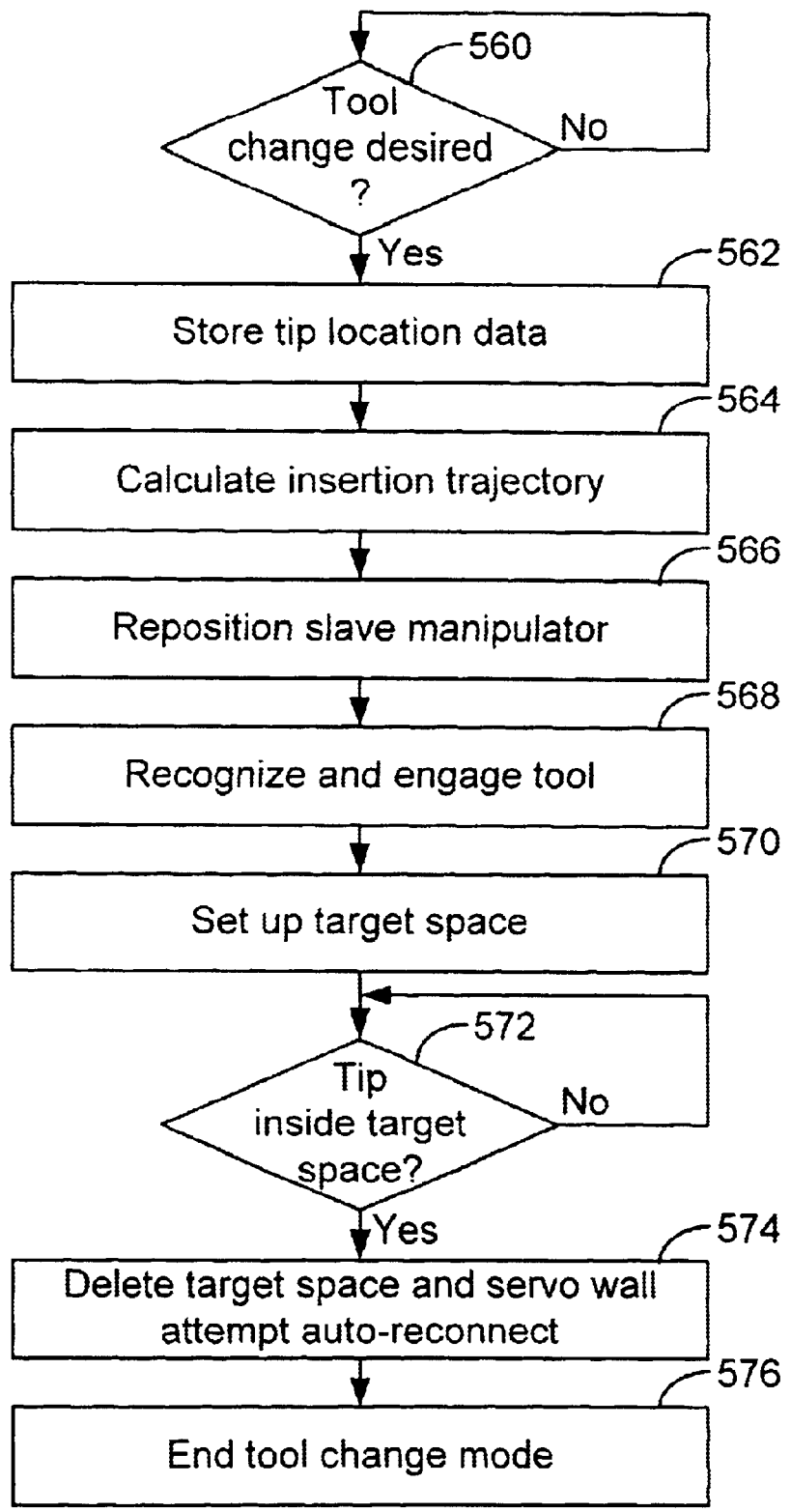
FIG. 5 is a flow diagram illustrating the guided tool change operation according to an embodiment of the present invention.

FIG. 5 is a flow diagram illustrating a preferred guided tool change operation performed using the subroutine 558. At the start of the tool change operation, the subroutine determines if tool change is desired (step 560). This may be indicated by, for example, the surgeon's pressing a button, a tool's being removed, etc. If tool change is desired, the subroutine stores the tip location data of the first tool just prior to its withdrawal from the surgical site (step 562). This can occur while the first tool is still in position or after it has been actually withdrawn. The subroutine may also store other information about the state of the first tool or the like, as needed by later computations. Based on the positioning data of the slave recorded in step 562 before tool withdrawal and the dimensions and configuration of the first tool 500, the subroutine 558 typically calculates the coordinates of the distal end 506 of the first tool 500 in relation to a reference point such as the port of entry 509. The calculation may be non-trivial when, for instance, the wrist of the first tool is bent (see FIG. 1), so that different joint angles and positions have to be taken into account. As shown in FIGS. 1 and 2, the insertion path that is calculated for the second tool 510 is the path 520 while the shaft 502 of the first tool 500 prior to withdrawal is aligned with the path 525. In a specific embodiment, the reference point is located at the point of entry 509 into the patient's body, as shown in FIGS. 1–3. The dimensions and configuration of the first tool 500 will typically be stored in advance in the memory 538 and retrieved by the subroutine 558, or they may alternatively be entered using the user interface 540.

In step 564, the subroutine 558 calculates the insertion or guide trajectory of the new tool. The subroutine typically calculates the position of the tool mount of the slave manipulator 530 which, when engaged with the new tool 510, will allow the new tool 510 to begin to be introduced into the surgical site 508 along a specified path, such as a straight line path along the imaginary line or insertion axis 520, so that the new tool path will intersect the location previously occupied by the first tool's end effector. The calculated position is then used to operate the controller 534 to reposition the tool mount. The parameters used to reposition the tool mount on the slave manipulator 530 may include, for example, coordinates of specific points and joint angles of specific joints between linkages contained in the slave manipulator 530 and the second tool 510. In a specific example, the parameters used to reposition the tool mount include outer pitch (OP) angle and outer yaw (OY) angle relative to a reference frame for introducing the tool 510 along the IO axis 520. The outer pitch and outer yaw for the second tool 510 will generally be different from the outer pitch and outer yaw for the first tool 500 in the operating position prior to its removal. In step 566, the slave manipulator 530 is repositioned to adjust the guide trajectory for the new tool, for instance, by repointing the robotic arm of the slave manipulator 530 to achieve the calculated OP and OY.

The next step in the guided tool change operation is to recognize and engage the new tool (step 568). The new tool will typically be different from the first tool, although they may be the same tool in some cases. The subroutine may retrieve data on the second tool 510 from the memory 538 via a readable memory chip, which is described in U.S. application Ser. No. 09/418,726, entitled "Surgical Robotic Tools, Data Architecture, and Use", filed on Oct. 15, 1999, which is fully incorporated herein by reference. Alternatively, the dimensions and other data of the second tool 510 may be entered via the user interface 540. The slave sensors 532 may be used to detect engagement between the second tool 510 and the slave manipulator 530 to ensure proper engagement before the introduction process is performed. The slave manipulator 530 has already been repositioned so that when it is engaged with the proximal end of the second tool 510, the tool is introduced into the surgical site 508 through the port of entry 509 along a predetermined path, for instance, along the 10 axis 520. The controller 534 directs the slave manipulator 530 to float the degree of freedom of movement along the IO axis 520 to allow the second tool 510 to move into the surgical site 508, either by a surgeon's assistant or by the controller itself causing the tool to move along the path.

Once the second tool is identified and the system understands the second tool's operating parameters and/or its geometry, the subroutine then sets up the target space 524 and servo wall 526 (FIG. 3) in step 570 based on criteria specified by a user, for instance, as discussed above. The criteria are typically stored internally in the memory 538, but they may be specified via the user interface 540 in alternate embodiments.

The new tool is introduced into the surgical site until the tip reaches the target space 524 (step 572). The introduction of the second tool 510 is typically performed by an operator, either by direct manual operation, or using a joystick or other interface, or remotely from the console or the like, or by the surgeon via the master manipulator 542, but may alternatively be at least partially or completely carried out by the system. The introduction of the second tool 510 may be carried out in any suitable manner. The second tool 510 follows the predetermined path such as the straight line path along the insertion axis 520. The system monitors the position of the tool tip in step 572 until it reaches the target space 524. When the distal end 516 of the tool 510 reaches the target space 524, the slave manipulator 530 encounters resistance by the system to halts movement of the tool 510. In step 574, the target space 524 and servo wall 526 are deleted. The tool change subroutine 558 may conclude by directing the controller 534 to reconnect the master manipulator 542 with the slave manipulator 530. The controller 534 may also activate the master manipulator 542 to align with the new position of the slave manipulator 530 and second tool 510 (step 572). Upon alignment, the operation switches from the guided tool change mode to the mapping mode so that the movement of the slave manipulator 530 and tool 510 follow the movement of the master manipulator 542 to allow the surgical procedure to resume with the second tool 510 (step 574). This mode switch may occur automatically or manually via user interface input. The tool change mode ends in step 576.

In some cases, an obstacle such as an organ may be present in the calculated insertion path such as the IO axis 520. The robotic system desirably provides the option to override the automatic process of guiding the second tool 510 so that an operator may manually maneuver the tool around the obstacle by pressing a clutch button or the like to switch the system from auto mode to manual mode so that the manipulator arm and tool may be maneuvered to avoid the body part. Alternatively, the determination of the insertion path takes into account obstacles and automatically produces a guide path that avoids those obstacles.

II. Exemplary Telesurgical System

The present invention may be used with any suitable robotic surgical system. For illustrative purposes, one exemplary system is illustrated in FIGS. 6A–11E, including an operator station (FIG. 6A), a slave manipulator (FIGS. 6B–7B), a surgical tool (FIGS. 8–10), and a master manipulator (FIGS. 11A–11E).

FIG. 6A shows an operator station or surgeon's console 200 of a minimally invasive telesurgical system. The station 200 includes a viewer 202 where an image of a surgical site is displayed in use. A support 204 is provided on which an operator, typically a surgeon, can rest his or her forearms while gripping two master controls (not shown in FIG. 6A), one in each hand. The master controls are positioned in a space 206 inwardly beyond the support 204. When using the control station 200, the surgeon typically sits in a chair in front of the control station 200, positions his or her eyes in front of the viewer 202 and grips the master controls one in each hand while resting his or her forearms on the support 204.

FIG. 6B shows a cart or surgical station 300 of the telesurgical system. In use, the cart 300 is positioned close to a patient requiring surgery and is then normally caused to remain stationary until a surgical procedure to be performed has been completed. The cart 300 typically has wheels or castors to render it mobile. The station 200 is typically positioned remote from the cart 300 and can be separated from the cart 300 by a great distance, even miles away, but will typically be used within an operating room with the cart 300.

The cart 300 typically carries three robotic arm assemblies. One of the robotic arm assemblies, indicated by reference numeral 302, is arranged to hold an image capturing device 304, e.g., an endoscope, or the like. Each of the two other arm assemblies 10 respectively, includes a surgical instrument 14. The endoscope 304 has a viewing end 306 at a remote end of an elongate shaft thereof. It will be appreciated that the endoscope 304 has an elongate shaft to permit its viewing end 306 to be inserted through an entry port into an internal surgical site of a patient's body. The endoscope 304 is operatively connected to the viewer 202 to display an image captured at its viewing end 306 on the viewer 202. Each robotic arm assembly 10 is normally operatively connected to one of the master controls. Thus, the movement of the robotic arm assemblies 10 is controlled by manipulation of the master controls. The instruments 14 of the robotic arm assemblies 10 have end effectors that are mounted on wrist members which are pivotally mounted on distal ends of elongate shafts of the instruments 14, as is described in greater detail below. It will be appreciated that the instruments 14 have elongate shafts to permit the end effectors to be inserted through entry ports into the internal surgical site of a patient's body. Movement of the end effectors relative to the ends of the shafts of the instruments 14 is also controlled by the master controls.

The robotic arms 10, 10, 302 are mounted on a carriage 97 by means of setup joint arms 95. The carriage 97 can be adjusted selectively to vary its height relative to a base 99 of the cart 300, as indicated by arrows K. The setup joint arms 95 are arranged to enable the lateral positions and orientations of the arms 10, 10, 302 to be varied relative to a vertically extending column 93 of the cart 300. Accordingly, the positions, orientations and heights of the arms 10, 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position.

Figure 7A:
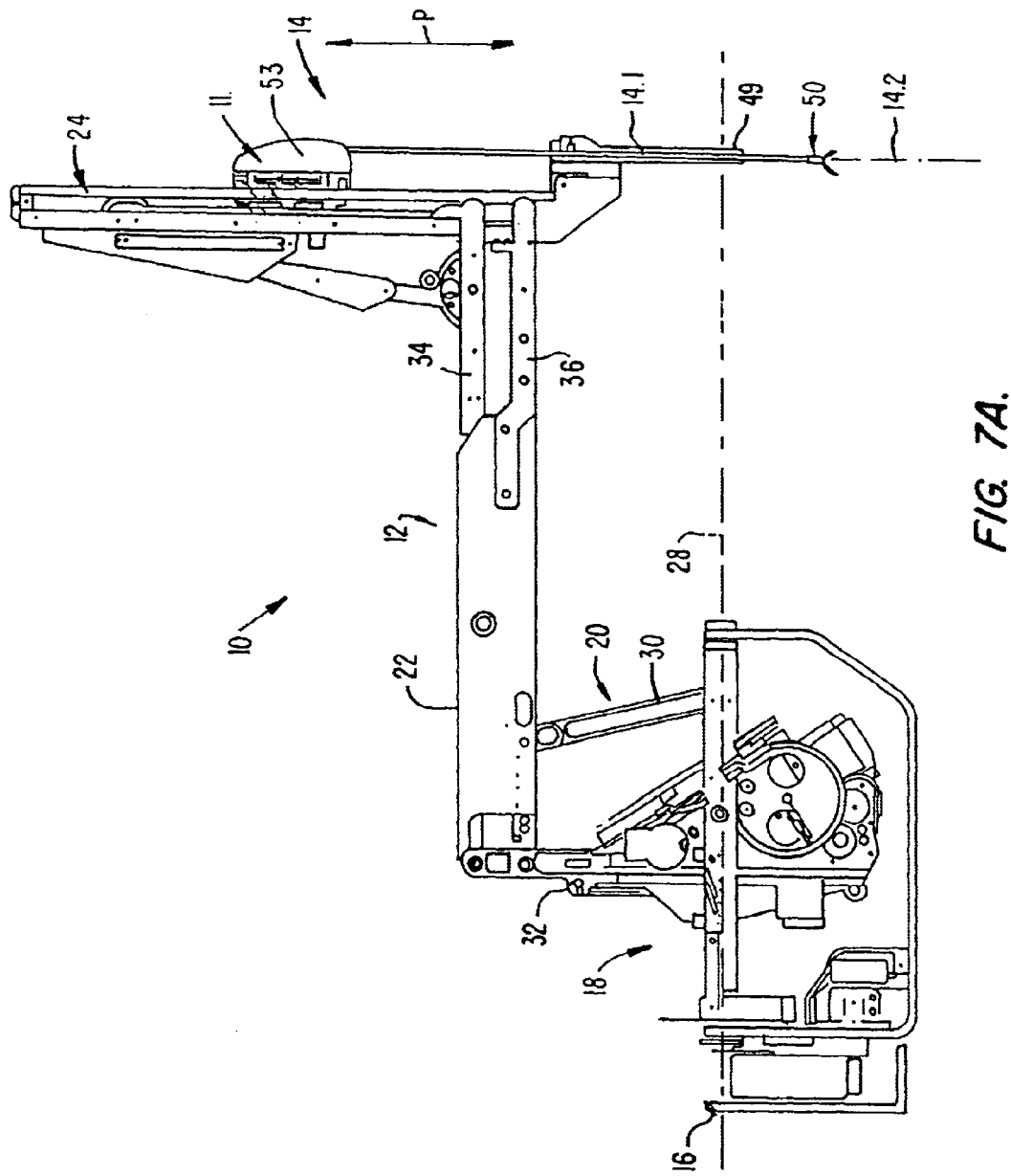
FIG. 7A is a side view of a robotic arm and surgical instrument assembly according to an embodiment of the invention.
Figure 7B:
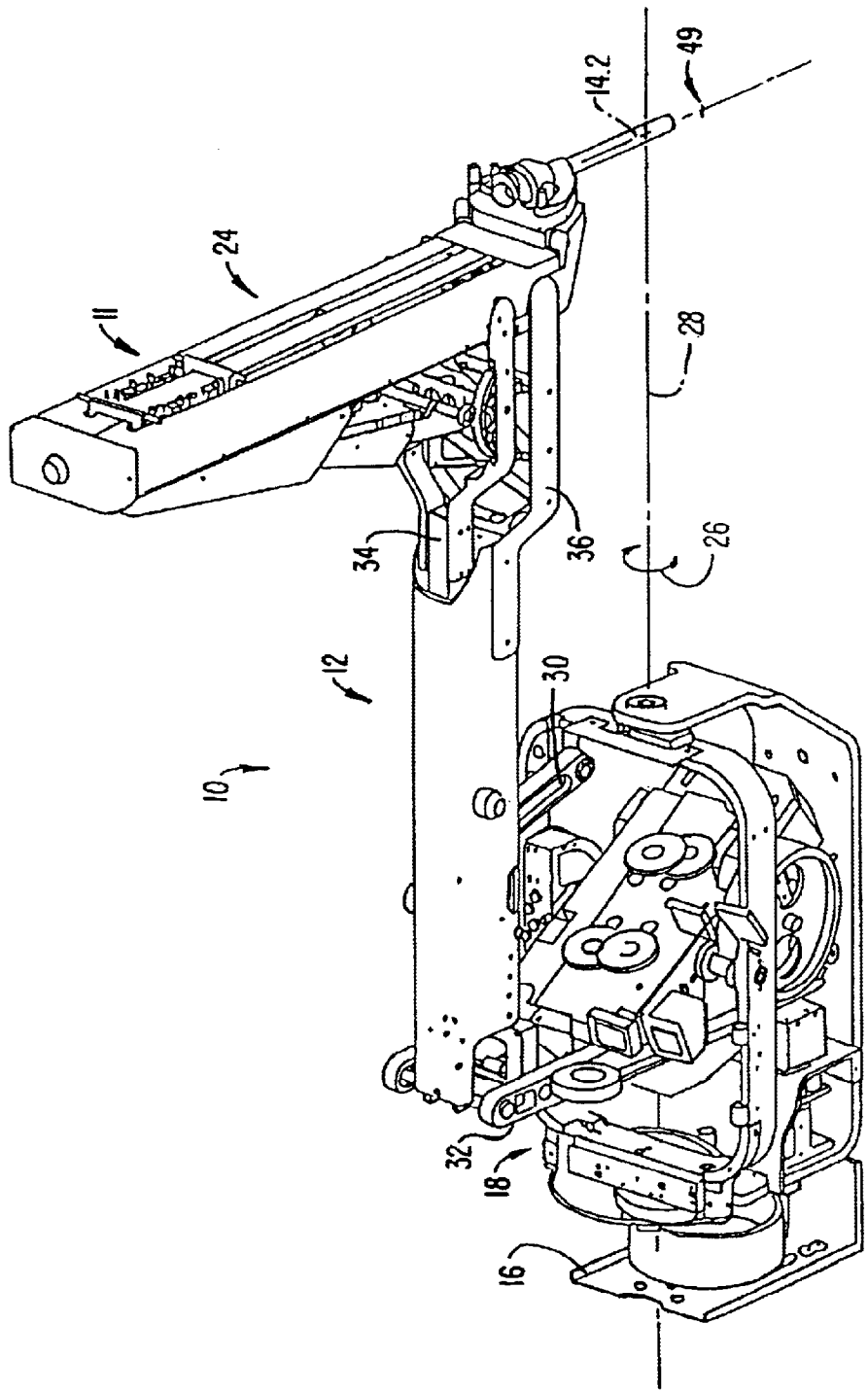
FIG. 7B is a perspective view of the robotic arm and surgical instrument assembly of FIG. 7A.
Figure 8:
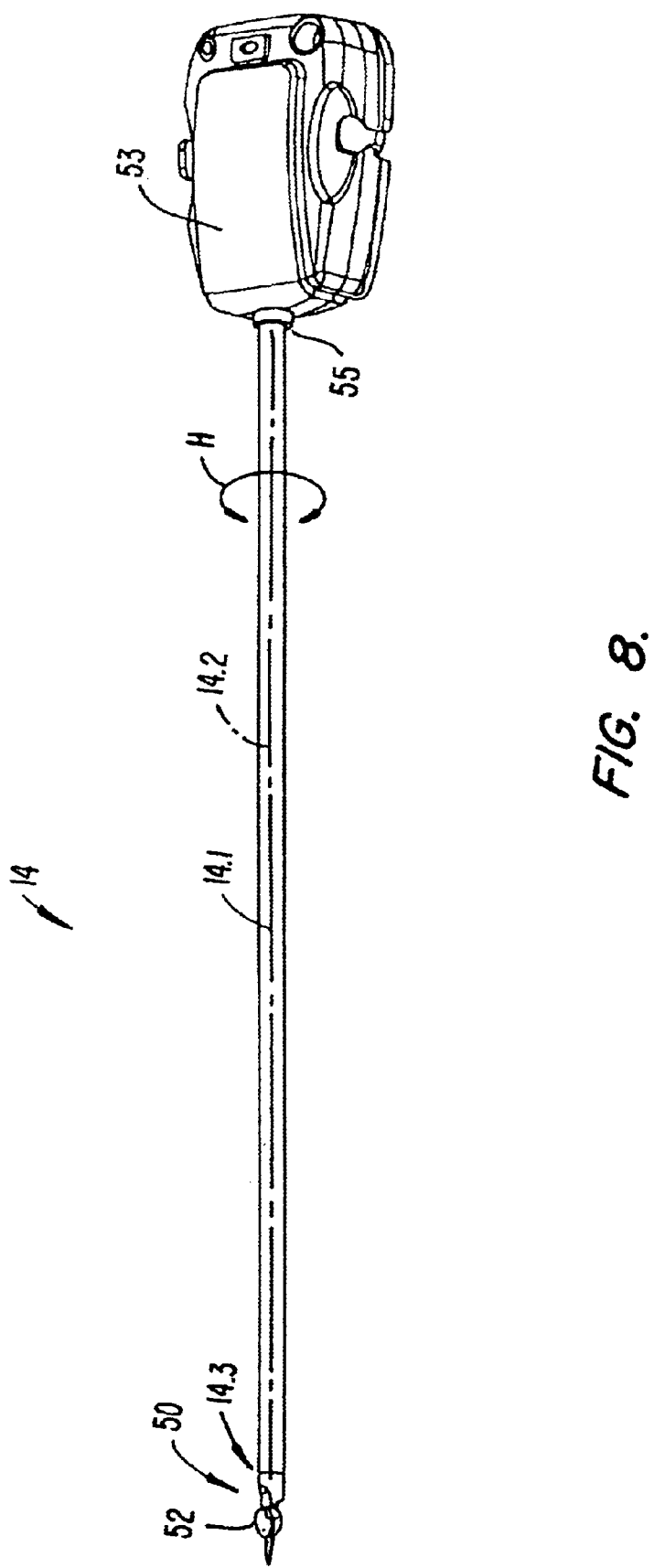
FIG. 8 is a perspective view of a surgical instrument according to an embodiment of the invention.

As shown in FIGS. 7A and 7B, each robotic arm assembly 10 includes an articulated robotic arm 12 and a surgical instrument 14 mounted thereon. As best seen in FIG. 8, the surgical instrument 14 includes an elongate shaft 14.1 and a wrist-like mechanism 50 located at a working end of the shaft 14.1. A housing 53, arranged releasably to couple the instrument 14 to the robotic arm 12, is located at an opposed end of the shaft 14.1. The shaft 14.1 is rotatably coupled to the housing 53 at 55 to enable angular displacement of the shaft 14.1 relative to the housing 53 as indicated by arrows H. In FIG. 7A, and when the instrument 14 is coupled or mounted on the robotic arm 12, the shaft 14.1 extends along an axis 14.2. The instrument 14 typically is releasably mounted on a carriage 11, which can be driven to translate along a linear guide formation 24 of the arm 12 in the direction of arrows P. This is referred to as the IO and in/out movement. The housing 53 includes spools that are rotatable to control cables to actuate linkages of the end effector 58, as described in U.S. provisional application Ser. No. 09/398, 958, entitled "Surgical Tools for Use in Minimally Invasive Telesurgical Applications", filed on Sep. 17, 1999, which is fully incorporated herein by reference. The robotic arm 12 includes disks for coupling with the spools to drive the spools upon connection of the instrument 14 to the robotic arm 12.

The robotic arm 12 is typically mounted on a base or platform at an end of its associated setup joint arm 95 by a bracket or mounting plate 16. The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle 18 in the direction of arrows 26 about a pivot axis 28 (FIG. 7B). The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to constrain the robotic arm 12 to move in a specific manner.

Figure 9:
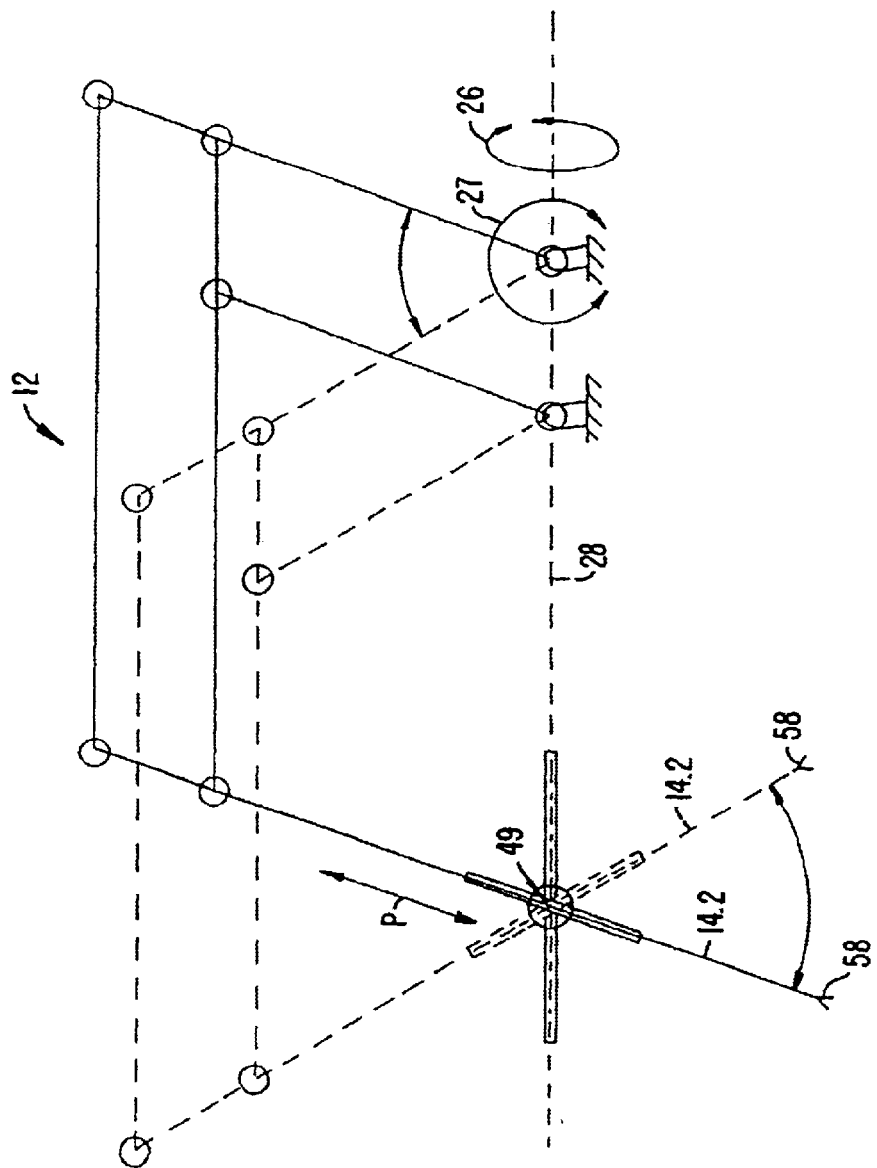
FIG. 9 is a schematic kinematic diagram corresponding to the side view of the robotic arm shown in FIG. 7A, and indicates the arm having been displaced from one position into another position.

The movements of the robotic arm 12 are illustrated schematically in FIG. 9. The solid lines schematically indicate one position of the robotic arm and the dashed lines indicate another possible position into which the arm can be displaced from the position indicated in solid lines.

It will be understood that the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in the same position relative to the stationary cart 300 on which the arm 12 is mounted. In use, the pivot center 49 is positioned at a port of entry into a patient's body when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively affect the surrounding tissue at the port of entry.

As can best be seen in FIG. 9, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27 and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control. Appropriately positioned sensors, e.g., potentiometers, encoders, or the like, are provided on the arm and its associated setup joint arm 95 to enable a control system of the minimally invasive telesurgical system to determine joint positions, as described in greater detail below. The term "sensors" as used herein is to be interpreted widely to include any appropriate sensors such as positional sensors, velocity sensors, or the like. By causing the robotic arm 12 selectively to displace from one position to another, the general position of the wrist-like mechanism 50 at the surgical site can be varied during the performance of a surgical procedure.

Figure 10:
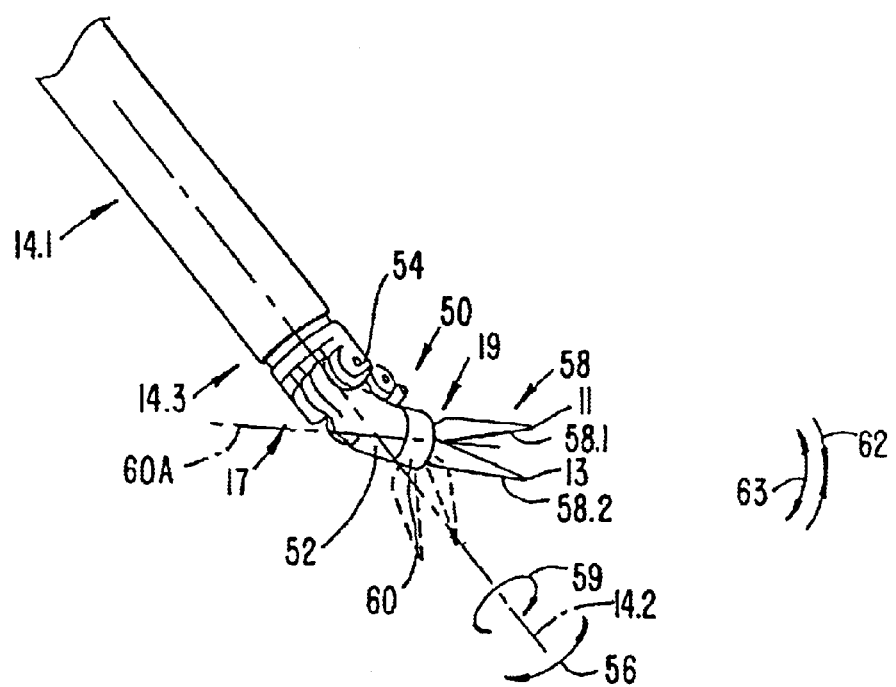
FIG. 10 is a perspective view of a wrist member and end effector of the surgical instrument shown in FIG. 8, the wrist member and end effector being movably mounted on a working end of a shaft of the surgical instrument.

Referring now to the wrist-like mechanism 50 of FIG. 10, the working end of the shaft 14.1 is indicated at 14.3. The wrist-like mechanism 50 includes a wrist member 52. One end portion of the wrist member 52 is pivotally mounted in a clevis 17 on the end 14.3 of the shaft 14.1 by means of a pivotal connection 54. The wrist member 52 can pivot in the direction of arrows 56 about the pivotal connection 54. An end effector 58 is pivotally mounted on an opposed end of the wrist member 52. The end effector 58 has two parts 58.1, 58.2 together defining a jaw-like arrangement.

The end effector can be in the form of any desired surgical tool, e.g., having two members or fingers which pivot relative to each other, such as a clip applier for anchoring clips, scissors, two-fingered blunt dissection tools, forceps, pliers for use as needle drivers, or the like. Moreover, it can include a single working member, e.g., a scalpel, cautery electrode, or the like. When a different tool is desired during the surgical procedure, the tool 14 is simply removed from its associated arm and replaced with an instrument bearing the desired end effector.

In FIG. 10, the end effector 58 is a gripper. The end effector 58 is pivotally mounted in a clevis 19 on an opposed end of the wrist member 52, by means of a pivotal connection 60. The free ends 11, 13 of the parts 58.1, 58.2 are angularly displaceable about the pivotal connection 60 toward and away from each other as indicated by arrows 62, 63. The members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 10. Furthermore, the shaft 14.1 is rotatably mounted on the housing 53 for rotation as indicated by the arrows 59. Thus, the end effector 58 has three degrees of freedom of movement relative to the arm 12 in addition to actuation of the end effector members to, e.g., grip tissue, namely, rotation about the axis 14.2 as indicated by arrows 59, angular displacement as a whole about the pivot 60 and angular displacement about the pivot 54 as indicated by arrows 56. By moving the end effector within its three degrees of freedom of movement, its orientation relative to the end 14.3 of the shaft 14.1 can selectively be varied. The movement of the end effector relative to the end 14.3 of the shaft 14.1 is controlled by appropriately positioned actuators, e.g., electrical motors, or the like, which respond to inputs from the associated master control to drive the end effector 58 to a desired orientation as dictated by movement of the master control. Furthermore, appropriately positioned sensors, e.g., encoders, or potentiometers, or the like, are provided to permit the control system of the minimally invasive telesurgical system to determine joint positions.

Figure 11A:
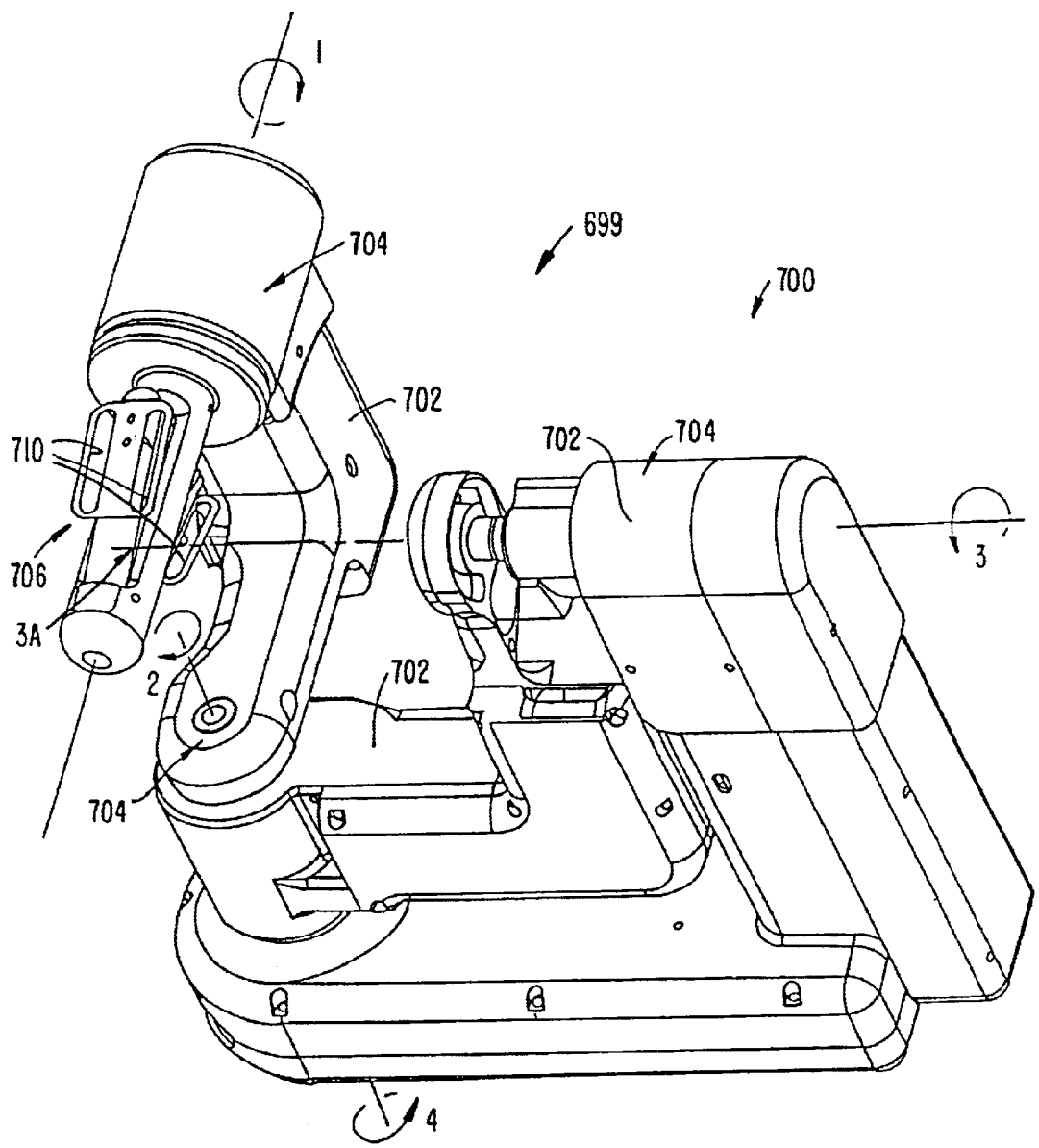
FIG. 11A is a perspective view of a hand held part or wrist gimbal of a master control device of the telesurgical system.
Figure 11B:
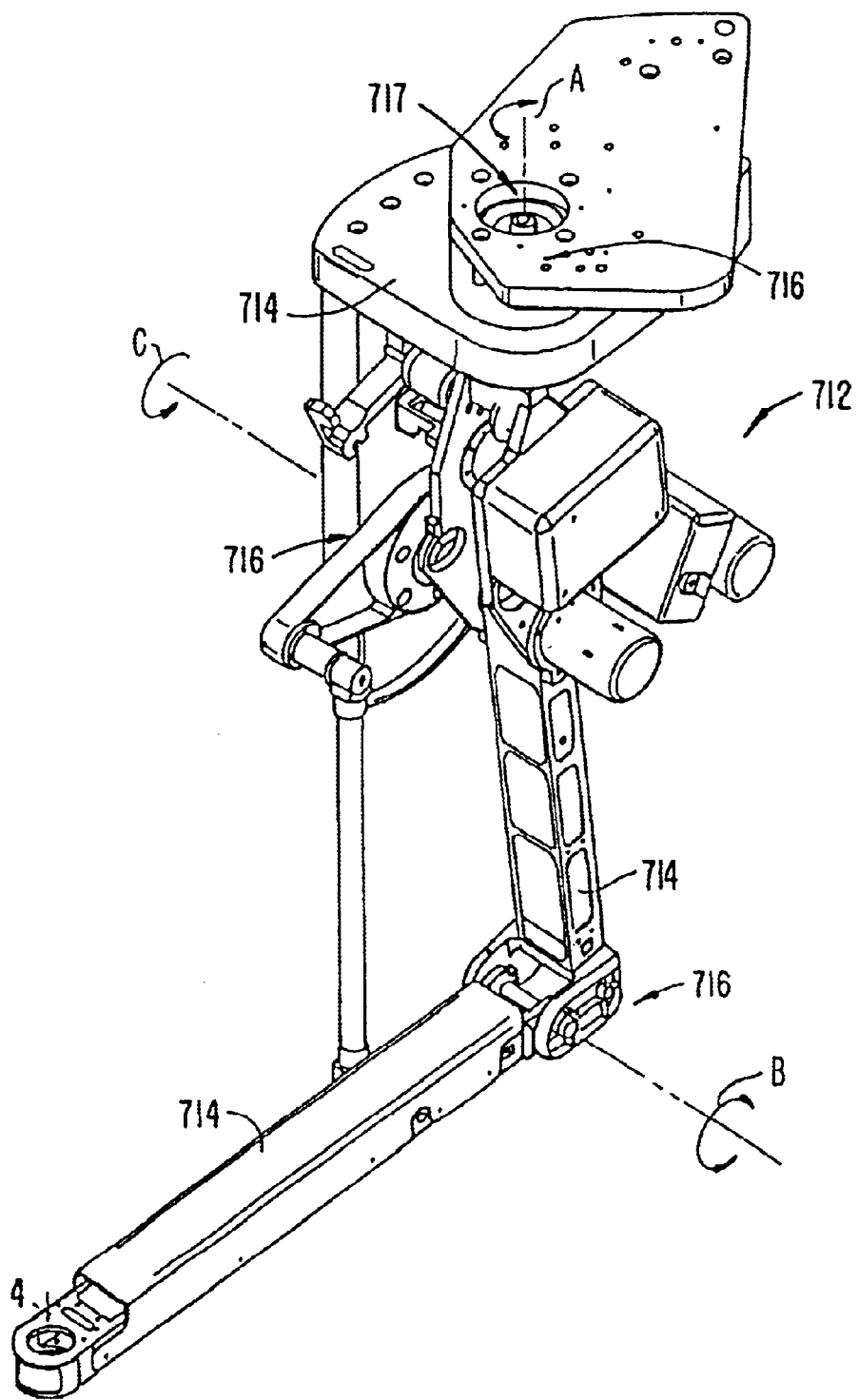
FIG. 11B is a perspective view of an articulated arm portion of the master control device of the telesurgical system on which the wrist gimbal of FIG. 11A is mounted in use.
Figure 11C:
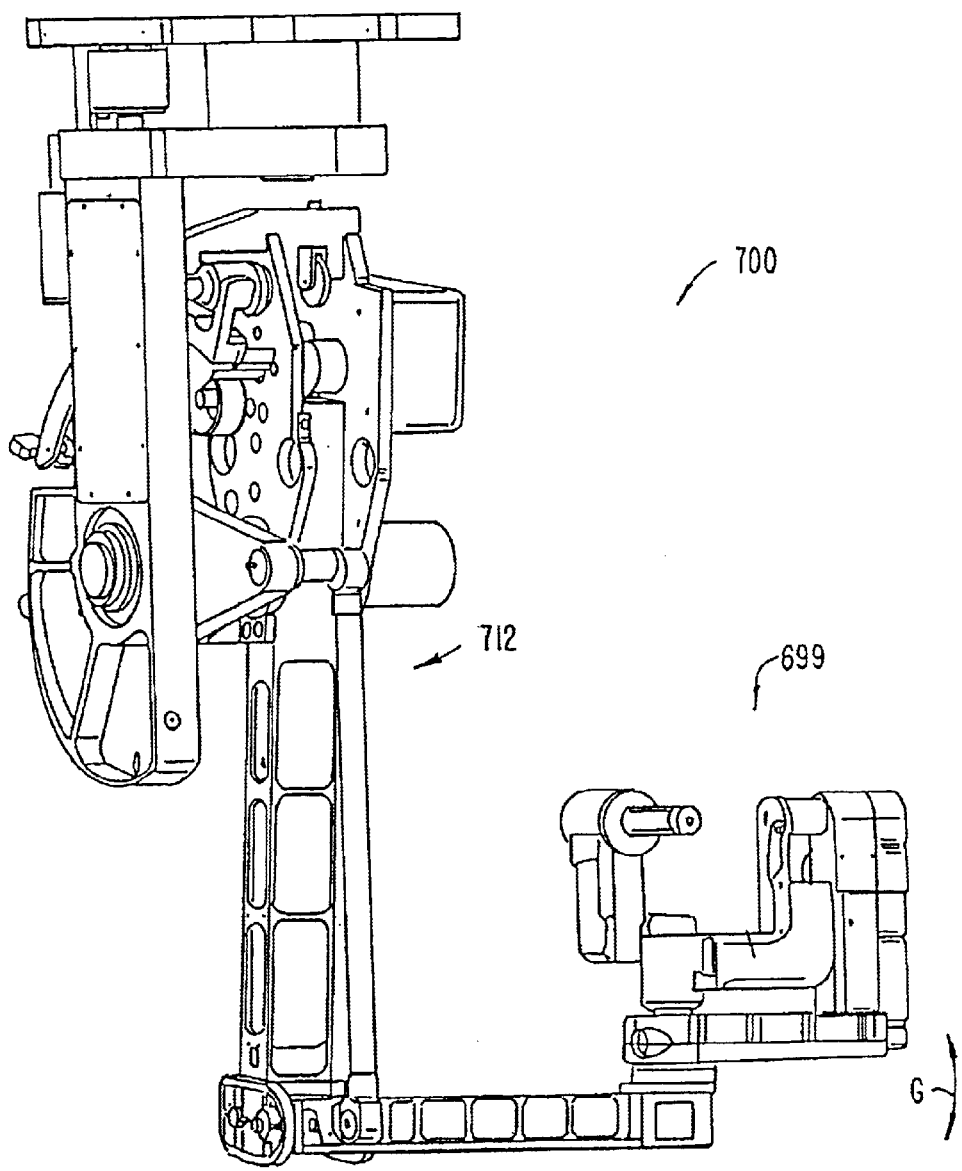
FIG. 11C is a perspective view of the master control device showing the wrist gimbal of FIG. 11A mounted on the articulated arm portion of FIG. 11B.

One of the master controls 700 is shown in FIG. 11C. As seen in FIG. 11A, a hand held part or wrist gimbal 699 of the master control device 700 has an articulated arm portion including a plurality of members or links 702 connected together by pivotal connections or joints 704. The surgeon grips the part 699 by positioning his or her thumb and index finger over a pincher formation 706. The surgeon's thumb and index finger are typically held on the pincher formation 706 by straps (not shown) threaded through slots 710. When the pincher formation 706 is squeezed between the thumb and index finger, the fingers or end effector elements of the end effector 58 close. When the thumb and index finger are moved apart the fingers of the end effector 58 move apart in sympathy with the moving apart of the pincher formation 706. The joints of the part 699 are operatively connected to actuators, e.g., electric motors, or the like, to provide for, e.g., force feedback, gravity compensation, and/or the like. Furthermore, appropriately positioned sensors, e.g., encoders, or potentiometers, or the like, are positioned on each joint 704 of the part 699, so as to enable joint positions of the part 699 to be determined by the control system.

The part 699 is typically mounted on an articulated arm 712 as indicated in FIG. 11B. Reference numeral 4 in FIGS. 11A and 11B indicates the positions at which the part 699 and the articulated arm 712 are connected together. When connected together, the part 699 can displace angularly about an axis at 4.

The articulated arm 712 includes a plurality of links 714 connected together at pivotal connections or joints 716. The articulated arm 712 further has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints 716 so as to enable joint positions of the articulated arm 712 to be determined by the control system.

To move the orientation of the end effector 58 and/or its position along a translational path, the surgeon simply moves the pincher formation 706 to cause the end effector 58 to move to where he wants the end effector 58 to be in the image viewed in the viewer 202. Thus, the end effector position and/or orientation is caused to follow that of the pincher formation 706.

The master control devices 700, 700 are typically mounted on the station 200 through pivotal connections at 717 as indicated in FIG. 11B. As mentioned above, to manipulate each master control device 700, the surgeon positions his or her thumb and index finger over the pincher formation 706. The pincher formation 706 is positioned at a free end of the part 699 which in turn is mounted on a free end of the articulated arm portion 712.

The electric motors and sensors associated with the robotic arms 12 and the surgical instruments 14 mounted thereon, and the electric motors and sensors associated with the master control devices 700 are operatively linked in the control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback. An example of a suitable control system is described in U.S. application Ser. No. 09/373,678, entitled "Camera Referenced Control in a Minimally Invasive Surgical Apparatus", filed on Aug. 13, 1999.

The above-described arrangements of apparatus and methods are merely illustrative of applications of the principles of this invention and many other embodiments and modifications may be made without departing from the spirit and scope of the invention as defined in the claims. For instance, other telesurgical systems, e.g., without a remote center of motion, can be used. Moreover, the present invention may be used for reintroducing the same tool after its removal from the surgical site without a tool change to return the tool to the original operating position. The determination of the target space and insertion depth may be varied. For instance, the operator may specify that the insertion of the new tool after a tool change into the surgical space to stop short by a preset amount on the insertion path to provide a safety zone. Although the target space is defined with reference to the instrument tip in the examples described above, it is understood that another portion of the tool may be used as a point of reference in other embodiments. The scope of the invention should, therefore, be determined not with reference to the above description, but instead should be determined with reference to the appended claims along with their full scope of equivalents.

What is claimed is:

1. A method of performing minimally invasive robotic surgery in a body cavity of a patient, the method comprising:
   recording an operating position at which the first robotic surgical tool is disposed inside the cavity, the first robotic surgical tool being configured to effect a treatment of a tissue in the cavity;
   removing the first robotic surgical tool from the cavity;
   determining the desired location within the body cavity of a second robotic surgical tool based on the recorded position of the first robotic tool;
   introducing the second robotic surgical tool into the cavity; and
   guiding the second robotic surgical tool to the desired location in close proximity to the operating position.

2. The method of claim 1 wherein recording the operating position of the first robotic surgical tool comprises determining a position of the distal end of the first robotic surgical tool just before the first tool is removed from the cavity.

3. The method of claim 2 wherein the second robotic surgical tool is guided to a target space comprising the recorded position of the first tool's distal end, said target space defined in part by said recorded position.

4. The method of claim 3 wherein the second robotic surgical tool is guided to a location at which a distal end of the second robotic surgical tool is disposed within a preset distance from the sensed position of the distal end of the first robotic surgical tool.

5. The method of claim 3 wherein the target space is defined to include a maximum allowable depth, said depth limiting the depth of insertion of the distal end of the second robotic surgical tool into the cavity from a port of entry of the cavity.

6. The method of claim 3 wherein the target space is determined by taking into account differences in configurations and dimensions between the first and second robotic surgical tools.

7. The method of claim 1 wherein the second robotic surgical tool is guided along a preset insertion path into the cavity to the location in close proximity to the operating position.

8. The method of claim 7 wherein the preset insertion path along which the second robotic surgical tool is guided into the cavity is substantially a straight line from a port of entry of the cavity to the target space.

9. The method of claim 7 further comprising automatically positioning the robotic arm outside the body cavity before introducing the second robotic surgical tool into the cavity so as to enable the second robotic surgical tool to be guided along the preset insertion path into the cavity to the location in close proximity to the operating position.

10. A method of performing minimally invasive robotic surgery in a body cavity of a patient, the method comprising:
    recording an operating position at which the first robotic surgical tool is disposed inside the cavity, the first robotic surgical tool being configured to effect a treatment of a tissue in the cavity;
    decoupling the first robotic surgical tool from a slave manipulator and removing the first robotic surgical tool from the cavity;
    determining the desired position within the body cavity of a second robotic tool based on the recorded position of the first robotic tool;
    coupling the second robotic surgical tool with the slave manipulator;
    introducing the second robotic surgical tool into the cavity; and
    guiding the second robotic surgical tool to the desired position in close proximity to the operating position.

11. The method of claim 10 further comprising deriving a target space to place the second robotic surgical tool based on the recorded operating position of the first robotic surgical tool, wherein the second robotic surgical tool is guided to within the target space.

12. The method of claim 10 wherein the second robotic surgical tool is guided to a location at which a distal end of the second robotic surgical tool disposed within a target space defined with respect to a location of a distal end of the first robotic surgical tool in the operating position.

13. The method of claim 12 further comprising deriving control parameters for controlling the slave manipulator based on the configurations and dimensions of the second robotic surgical tool, wherein said guiding the second robotic surgical tool to the target space comprises defining the target space using the derived control parameters.

14. The method of claim 12 wherein the slave manipulator is operatively disconnected from a master manipulator during introducing and guiding of the second robotic surgical tool, further comprising operatively connecting the slave manipulator with the master manipulator when the second robotic tool enters the target space.

15. The method of claim 10 wherein the second robotic surgical tool is guided along a preset insertion path into the cavity to the location in close proximity to the operating position.

16. The method of claim 10 wherein the slave manipulator is operatively disconnected from a master manipulator during introducing and guiding of the second robotic surgical tool, further comprising operatively connecting the slave manipulator with the master manipulator when the second robotic surgical tool reaches the location in close proximity to the operating position so that movement of the slave manipulator is mapped to movement of the master manipulator.

17. The method of claim 10 wherein said recording said operating position at which said first robotic surgical tool is disposed inside the cavity is performed after said first robotic surgical tool is decoupled from said slave manipulator and removed from said cavity.

18. A surgical robotic system comprising: a slave manipulator for coupling with and actuating a robotic surgical tool inside a body cavity of a patient;
 a controller configured to control movement of the slave manipulator and the robotic tool;
 at least one sensor coupled with the slave manipulator and the controller for sensing an operating position of the robotic surgical tool coupled with the slave manipulator;
 said controller comprising a computer, said computer having a first set of computer instructions for controlling the slave manipulator, after the first robotic surgical tool is removed from the cavity and decoupled from the slave manipulator, to automatically position the slave manipulator so that the second robotic surgical tool can be guided to a location in close proximity to the sensed operating position, the first robotic surgical tool being configured to effect a treatment of a tissue in the cavity.

19. The surgical robotic system of claim 18 wherein said slave manipulator is automatically positioned before the second robotic surgical tool is coupled with the slave manipulator.

20. The surgical robotic system of claim 18 wherein the computer comprises a second set of computer instructions for deriving a target space to place the second robotic surgical tool based on the operating position of the first robotic surgical tool.

21. The surgical robotic system of claim 18 wherein the computer comprises a second set of computer instructions for calculating, based on the operating position of the distal end of the first robotic surgical tool, a maximum allowable depth limiting depth of insertion of the distal end of the second robotic surgical tool into the cavity from a port of entry of the cavity.

22. The surgical robotic system of claim 18 wherein the first set of computer instructions additionally controls the slave manipulator to automatically guide the second robotic surgical tool along a preset insertion path to a location in close proximity to the sensed operating position.

23. The surgical robotic system of claim 18 further comprising a master manipulator, wherein the computer-readable program includes a third set of computer instructions for operatively disconnecting the slave manipulator from the master manipulator during introducing and guiding of the second robotic surgical tool and for operatively connecting the slave manipulator with the master manipulator when the second robotic surgical tool reaches the location in close proximity to the operating position so that movement of the slave manipulator is mapped to movement of the master manipulator.

24. A method of delivering a robotic surgical instrument having a distal tip to a surgical site, comprising:
 determining, via a computer, a target space for a preset portion of the robotic surgical instrument to occupy upon delivery to the surgical site, based at least in part on a location in the surgical site previously occupied by another surgical instrument configured to effect a surgical treatment in the surgical site, wherein said location in the surgical site was sensed using a sensor during the surgical treatment by said another surgical instrument; and
 guiding delivery of the robotic surgical instrument to the surgical site such that the instrument is delivered into the target space.

25. The method of delivering of claim 24 wherein the preset portion of the robotic surgical instrument is a distal tip of the instrument.

26. The method of delivering of claim 25 wherein said target space is determined based at least in part on a sensed location previously occupied by a second surgical instrument having a tip, said location in the vicinity of the surgical site and previously occupied by said second surgical instrument tip immediately before removal of said instrument from said surgical site.

27. The method of delivering of claim 24 wherein said target space is determined based at least in part on information derived from the robotic surgical instrument to be delivered to the surgical site.

28. The method of delivering of claim 24 wherein said guiding delivery comprises guiding delivery of the instrument in one degree of freedom of movement along an insertion axis.

29. The method of delivering of claim 24 further comprising operatively coupling a master controller to a slave manipulator upon said instrument entering said target space, said surgical instrument coupled to said slave manipulator.

30. The method of delivering of claim 29 wherein said master controller is usable by an operator to control movement of the surgical instrument at the surgical site to manipulate tissue and perform surgery.

31. The method of delivering of claim 24 wherein said surgical instrument is coupled to a slave manipulator, wherein at least one degree of freedom of movement of said slave manipulator is constrained during instrument delivery, so as to facilitate guiding delivery of the instrument to the surgical site.

32. The method of delivering of claim 31 wherein said surgical instrument is manually guided to the surgical site by an operator.

33. The method of delivering of claim 24 wherein said instrument comprises a proximal shaft, a wrist member movably coupled to said shaft at a first joint, and an end effector movably coupled to said wrist member at a second joint, movement around said first and second joints providing said end effector with multiple degrees of freedom of movement relative to said shaft, said multiple degrees of freedom of movement constrained during delivery of said instrument to said surgical site.

* * * * *